United States Patent
Palacio et al.

(10) Patent No.: US 7,619,085 B2
(45) Date of Patent: Nov. 17, 2009

(54) PYROGLUTAMATE SALTS AND THEIR USE IN THE OPTICAL RESOLUTION OF INTERMEDIATES FOR THE SYNTHESIS OF DEXTROCETIRIZINE AND LEVOCETIRIZINE

(75) Inventors: Magali Palacio, Paris (FR); Celal Ates, Louvain-la-Neuve (BE)

(73) Assignee: UCB Pharma, S.A., Brussels (BE)

( * ) Notice: Subject to any disclaimer, the term of this patent is extended or adjusted under 35 U.S.C. 154(b) by 252 days.

(21) Appl. No.: 11/817,320

(22) PCT Filed: Feb. 23, 2006

(86) PCT No.: PCT/EP2006/001676

§ 371 (c)(1),
(2), (4) Date: Aug. 28, 2007

(87) PCT Pub. No.: WO2006/094648

PCT Pub. Date: Sep. 14, 2006

(65) Prior Publication Data

US 2008/0269489 A1    Oct. 30, 2008

(30) Foreign Application Priority Data

Mar. 3, 2005    (EP) ................... 05004653

(51) Int. Cl.
*C07D 295/14*    (2006.01)
(52) U.S. Cl. ................... 544/396; 514/255.04
(58) Field of Classification Search ........ None
See application file for complete search history.

(56) References Cited

U.S. PATENT DOCUMENTS 5,478,941 A * 12/1995 Cossement et al. ......... 544/383
2009/0143582 A1* 6/2009 Zhu ..................... 544/389

FOREIGN PATENT DOCUMENTS

GB       2225321   *  5/1990
WO    1994-06429 A1    3/1994

OTHER PUBLICATIONS

Pflum, Derek, A., "A Large-Scale Synthesis of Enantiomerically Pure Cetirizine Dihydrochloride Using Preparative Chiral HPLC," Organic Process Research & Development, 2001, pp. 110-115.

* cited by examiner

Primary Examiner—Emily Bernhardt
(74) Attorney, Agent, or Firm—McDonnell Boehnen Hulbert & Berghoff LLP

(57) ABSTRACT

The present invention relates to (S)-2-[4-(4-chlorobenzhydryl)piperazin-1-yl]-ethoxyacetamide-(S)-pyrrolidone-5-carboxylic acid salt; (R)-2-[4-(4-chlorobenzhydryl)piperazin-1-yl]-ethoxyacetamide-(S)-pyrrolidone-5-carboxylic acid salt; (S)-2-[4-(4-chlorobenzhydryl)piperazin-1-yl]-ethoxyacetamide-(R)-pyrrolidone-5-carboxylicacid salt; or (R)-2-[4-(4-chlorobenzhydryl)piperazin-1-yl]-ethoxycetamide-(R)-pyrrolidone-5-carboxylic salt. The present invention relates also to a process for preparing (S)-2-[4-(4-chlorobenzhydryl)piperazin-1-yl]-ethoxyacetamide (I) and (R)-2-[4-(4-chlorobenzhydryl) piperazin-1-yl]-ethoxyacetamide (II) by chemical resolution of a mixture. These compounds are respectively intermediates for the synthesis of dextrocetirizine and levocetirizine.

(I)

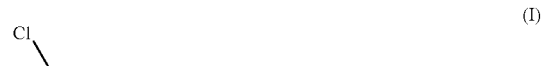

(II)

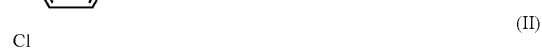

7 Claims, No Drawings

PYROGLUTAMATE SALTS AND THEIR USE IN THE OPTICAL RESOLUTION OF INTERMEDIATES FOR THE SYNTHESIS OF DEXTROCETIRIZINE AND LEVOCETIRIZINE

The present invention relates to new pyroglutamate salts and to their use as mouse synthesis intermediates, especially for the preparation of pharmaceutically active compounds.

The present invention relates also to a process for preparing, (S)-2-[4-(4-chloro benzhydryl)piperazin-1-yl]-ethoxy-acetamide and (R)-2-[4-(4-chlorobenzhydryl)piperazin-1-yl]-ethoxyacetamide corresponding respectively to formula I and formula II. (S)-2-[4-(4-chloro benzhydryl)piperazin-1-yl]-ethoxyacetamide and (R)-2-[4-(4-chlorobenzhydryl)piperazin-1-yl]-ethoxy acetamide are respectively intermediates for the synthesis of dextrocetirizine and levocetirizine

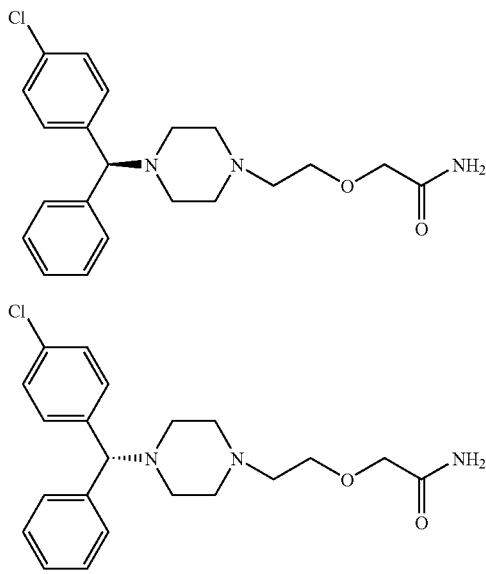

Processes for preparing levocetirizine and dextrocetirizine from its racemic mixture cetirizine ([2-[4-[(4-chlorophenyl)phenylmethyl]-1-piperazinyl]ethoxy]acetic acid) are known from Great Britain patents 2 225 320 and 2 225 321, and from European patent 0 663 828. Processes for preparing cetirizine, an individual optical isomer thereof or a pharmaceutically acceptable salt thereof have been described in European patent 0 058 146, Great Britain patents 2 225 320 and 2 225 321, U.S. Pat. No. 5,478,941, European patent applications 0 601 028 and 0 801 064 and international patent application WO 97/37982. GB 2,225,321 describes a process for the preparation of cetirizine in the levorotatory form, dextrorotatory form or a mixture thereof comprising the hydrolysis of enantiomerically pure or racemic [2-[4-[(4-chlorophenyl)phenylmethyl]-1-piperazinyl]ethoxy]-acetonitrile. WO 2004/065360 describes a process for the preparation of levocetirizine, wherein an enantiomeric pure intermediate is used.

Processes for preparing (S)-2-[4-(4-chlorobenzhydryl)piperazin-1-yl]-ethoxyacetamide and (R)-2-[4-(4-chlorobenzhydryl)piperazin-1-yl]-ethoxyacetamide are known from European patent 0 617 028.

Resolution of the enantiomers of cetirizine or precursors thereto using conventional means, such as an optical active resolving acid, is known (International application WO 94/06429). Resolution of 2-[4-(4-chlorobenzhydryl)piperazin-1-yl]-ethoxyacetamide by chiral HPLC is known (Organic Process Research and Development, vol. 5, 2001, pages 110-115).

We have now found an alternative, simpler process for preparing substantially enantiomerically pure compounds, such as levocetirizine, wherein a new substantially enantiomerically pure intermediate is used.

By "substantially enantiomerically pure" compound one should understand a compound which has an enantiomeric excess of at least 96%.

Surprisingly, it has been found that resolution by diastereomeric salt formation and crystallisation of these salts is a potential alternative which is easier to apply industrially, in order to obtain partially enriched mixture of and, at the end, substantially enantiomerically pure (S)-2-[4-(4-chlorobenzhydryl)piperazin-1-yl]-ethoxyacetamide and substantially enantiomerically pure (R)-2-[4-(4-chlorobenzhydryl)piperazin-1-yl]-ethoxyacetamide.

This technique can be transposed to the industrial scale to give, efficiently and with excellent production efficiency, a product having the required optical purity for a pharmaceutical application.

In a first aspect, the present invention relates to a compound selected from (S)-2-[4-(4-chlorobenzhydryl)piperazin-1-yl]-ethoxyacetamide-(S)-pyrrolidone-5-carboxylic acid salt; (R)-2-[4-(4-chlorobenzhydryl)piperazin-1-yl]-ethoxyacetamide-(S)-pyrrolidone-5-carboxylic acid salt; (S)-2-[4-(4-chlorobenzhydryl)piperazin-1-yl]-ethoxyacetamide-(R)-pyrrolidone-5-carboxylic acid salt; or (R)-2-[4-(4-chlorobenzhydryl)piperazin-1-yl]-ethoxyacetamide-(R)-pyrrolidone-5-carboxylic salt. These compounds may be partially diastereoisomerically enriched compounds or substantially diastereoisomerically pure compounds. By "substantially diastereoisomerically pure" compound one should understand a compound which has a diastereoisomeric excess of at least 96%.

In a preferred embodiment according to the invention the salts are substantially diastereisomerically pure compounds.

The compounds of the invention can be obtained by reaction of a mixture of (R)- and (S)-2-[4-(4-chlorobenzhydryl)piperazin-1-yl]-ethoxyacetamide with (S)-pyrrolidone-5-carboxylic acid (also named L-pyroglutamic acid) or (R)-pyrrolidone-5-carboxylic acid (also named D-pyroglutamic acid).

The mixture of enantiomers, for example (R)- and (S)-2-[4-(4-chlorobenzhydryl)piperazin-1-yl]-ethoxyacetamide, may be a racemic mixture of enantiomers or a partially enriched mixture of enantiomers.

By "racemic mixture" of enantiomers one should understand a mixture in which the molar ratio of enantiomers is equal to 1.

By "partially enriched mixture" of stereoisomers, one should understand a mixture in which the molar ratio of stereoisomers is greater than 1. Stereoisomers within the meaning of the present definition may be for example diastereisomers or enantiomers.

(S)-2-[4-(4-chlorobenzhydryl)piperazin-1-yl]-ethoxyacetamide-(S)-pyrrolidone-5-carboxylic acid salt; (R)-2-[4-(4-chlorobenzhydryl)piperazin-1-yl]-ethoxyacetamide-(S)-pyrrolidone-5-carboxylic acid salt; (S)-2-[4-(4-chlorobenzhydryl)piperazin-1-yl]-ethoxyacetamide-(R)-pyrrolidone-5-carboxylic acid salt; or (R)-2-[4-(4-chlorobenzhydryl)piperazin-1-yl]-ethoxyacetamide-(R)-pyrrolidone-5-carboxylic acid salt can be used for the synthesis of substantially enantiomerically pure cetirizine derivatives, respectively dextrocetirizine and levocetirizine synthesis.

In a second aspect, the present invention relates to the use of (S)-2-[4-(4-chlorobenzhydryl)piperazin-1-yl]-ethoxyacetamide-(S)-pyrrolidone-5-carboxylic acid salt; (R)-2-[4-(4-chlorobenzhydryl)piperazin-1-yl]-ethoxyacetamide-(S)-pyrrolidone-5-carboxylic acid salt; (S)-2-[4-(4-chlorobenzhydryl)piperazin-1-yl]-ethoxyacetamide-(R)-pyrrolidone-5-carboxylic acid salt; or (R)-2-[4-(4-chlorobenzhydryl)piperazin-1-yl]-ethoxyacetamide-(R)-pyrrolidone-5-carboxylic acid salt as synthesis intermediates, especially for the preparation of pharmaceutically active compounds.

According to another embodiment, the present invention relates to a process for preparing (S)-2-[4-(4-chlorobenzhydryl)piperazin-1-yl]-ethoxyacetamide and (R)-2-[4-(4-chlorobenzhydryl)piperazin-1-yl]-ethoxyacetamide, by chemical resolution of a racemic or partially enriched mixture of (R)- and (S)-2-[4-(4-chlorobenzhydryl)piperazin-1-yl]-ethoxyacetamide in the presence of (S)-pyrrolidone-5-carboxylic acid or (R)-pyrrolidone-5-carboxylic acid.

Usually chemical resolution of a racemic mixture of (R)- and (S)-2-[4-(4-chlorobenzhydryl)piperazin-1-yl]-ethoxyacetamide is achieved.

Preferably, the present invention relates to a process for preparing substantially enantiomerically pure (S)-2-[4-(4-chlorobenzhydryl)piperazin-1-yl]-ethoxyacetamide and substantially enantiomerically pure (R)-2-[4-(4-chlorobenzhydryl)piperazin-1-yl]-ethoxyacetamide. In the process of the invention (S)-pyrrolidone-5-carboxylic acid is preferably employed. Usually it is employed in an amount sufficient to allow the reaction to proceed.

Usually the resolution of a racemic mixture is achieved. Generally, the amount of the (S)-pyrrolidone-5-carboxylic acid is 0.1 to 4 moles per mole of the racemic mixture of (R)- and (S)-2-[4-(4-chlorobenzhydryl)piperazin-1-yl]-ethoxyacetamide. Preferably the amount is 0.4 to 1.5 in moles per moles. More preferably the amount is 0.75 to 1.25 in moles per moles. Best results have been obtained with an amount of (S)-pyrrolidone-5-carboxylic acid ranging from 0.9 to 1.1 in moles per moles of the racemic mixture of (R)- and (S)-2-[4-(4-chlorobenzhydryl)piperazin-1-yl]-ethoxyacetamide.

Usually the process according to the invention is performed in the presence of a solvent or a mixture of solvents. The solvent or mixture of solvents may be any solvent or mixture of solvents provided that said solvent or mixture of solvents does not take part in the reaction.

Generally, the solvent of the invention is an organic solvent. Usually the solvent of the invention is selected from water; alcohols, such as ethanol, methanol, isopropanol; ketones such as acetone, butan-2-one, methyl isobutyl ketone; ethers, such as, MTBE (methyl tert-butyl ether), THF (tetrahydrofuran); esters, such as AcOMe (methyl acetate), AcOEt (ethyl acetate), AcOiPr (isopropyl acetate); or a mixture of two or more of these solvents. Preferably the solvent of the invention is selected from ethyl acetate; THF; a mixture of ethyl acetate and methanol; a mixture of water and THF; a mixture of THF and methanol; or a mixture thereof. More preferably, the solvent of the invention is selected from ethyl acetate; THF; a mixture of ethyl acetate and methanol (4:1); a mixture of THF and methanol (4:1). Most preferred solvents of the invention are a mixture of ethyl acetate and methanol (4:1); and a mixture of THF and methanol (4:1). Best results have been obtained with a mixture of ethyl acetate and methanol (4:1) as solvent.

Generally, the amount of the solvent is 0.4 L to 8 L per mole of the 2-[4-(4-chlorobenzhydryl)piperazin-1-yl]-ethoxyacetamide. Preferably, the amount of the solvent is 1.0 L to 4 L per mole. More preferably, the amount of the solvent is 1.6 L to 2.8 L per mole. Best results have been obtained with an amount of the solvent of 1.2 L to 2.8 L per mol of the racemic mixture of (R)- and (S)-2-[4-(4-chlorobenzhydryl)piperazin-1-yl]-ethoxyacetamide.

In the process according to the invention, the temperature of contact is from ambient temperature to the boiling point of the solvent used.

The crystallisation may be spontaneous or initiated by seeding the reaction medium with substantially diastereoisomerically pure crystals of (S)-2-[4-(4-chlorobenzhydryl)piperazin-1-yl]-ethoxyacetamide-(S)-pyrrolidone-5-carboxylic acid salt; (R)-2-[4-(4-chlorobenzhydryl)piperazin-1-yl]-ethoxyacetamide-(S)-pyrrolidone-5-carboxylic acid salt; (S)-2-[4-(4-chlorobenzhydryl)piperazin-1-yl]-ethoxyacetamide-(R)-pyrrolidone-5-carboxylic acid salt; or (R)-2-[4-(4-chlorobenzhydryl)piperazin-1-yl]-ethoxyacetamide-(R)-pyrrolidone-5-carboxylic salt.

The substantially diastereisomerically pure salt or partially diastereoisomerically enriched salt obtained by crystallisation may optionally be recrystallised or treated by a similar method to further increase the enantiomeric excess of the active amide.

After the substantially diastereoisomerically pure salt is obtained, it may be decomposed by a suitable method to isolate substantially enantiomerically pure 2-[4-(4-chlorobenzhydryl)piperazin-1-yl]-ethoxyacetamide and the resolving agent or may be directly transformed into substantially enantiomerically pure cetirizine hydrochloride.

Any method may be used to decompose the substantially diastereoisomerically pure salt. For example, an aqueous solution containing the substantially diastereisomerically pure salt may be made alkaline and the substantially enantiomerically pure (R) or (S)-2-[4-(4-chlorobenzhydryl)piperazin-1-yl]-ethoxyacetamide can be extracted with a suitable organic solvent which separates it from the aqueous layer, followed by distilling off the organic solvent, thereby allowing the isolation of the substantially enantiomerically pure (R) or (S)-2-[4-(4-chlorobenzhydryl)piperazin-1-yl]-ethoxyacetamide.

The suitable solvent used for the extraction of the substantially enantiomerically pure (R) or (S)-2-[4-(4-chlorobenzhydryl)piperazin-1-yl]-ethoxyacetamide can be any non-water-miscible organic solvent such as toluene, ethyl acetate, dichloromethane.

According to an embodiment, the invention concerns a method for obtaining a partially diastereoisomerically enriched (S)-2-[4-(4-chlorobenzhydryl)piperazin-1-yl]-ethoxyacetamide-(S)-pyrrolidone-5-carboxylic acid salt or partially diastereoisomerically enriched (R)-2-[4-(4-chlorobenzhydryl)piperazin-1-yl]-ethoxyacetamide-(S)-pyrrolidone-5-carboxylic acid salt, comprising:

mixing a racemic or partially enriched mixture of (R)- and (S)-2-[4-(4-chlorobenzhydryl)piperazin-1-yl]-ethoxyacetamide with (S)-pyrrolidone-5-carboxylic acid in a solvent optionally heating the reaction medium to reflux;

allowing said reaction medium to cool;

separating a solid from the solution.

Preferably, the partially diastereoisomerically enriched salts according to the invention have a molar ratio of diastereoisomers which is greater than 2, more preferably greater than 3, most preferably greater than 4.

According to another embodiment, the invention concerns a method for obtaining a substantially diastereoisomerically pure (S)-2-[4-(4-chlorobenzhydryl)piperazin-1-yl]-ethoxyacetamide-(S)-pyrrolidone-5-carboxylic acid salt or partially diastereoisomerically enriched (R)-2-[4-(4-chlorobenzhydryl)piperazin-1-yl]-ethoxyacetamide-(S)-pyrrolidone-5-carboxylic acid salt comprising:

mixing a racemic or partially enriched mixture of 2-[4-(4-chlorobenzhydryl)piperazin-1-yl]-ethoxy acetamide with (S)-pyrrolidone-5-carboxylic acid in a solvent;
optionally heating the reaction medium to reflux;
allowing said reaction medium to cool;
separating a solid from the solution;
optionally recrystallising by:
optionally mixing the solid and a solvent;
optionally heating the reaction medium to reflux;
allowing said reaction medium to cool;
separating a solid from the solution;
drying the solid.

The recrystallisation step may be achieved as many times as the man skilled in the art will deem it necessary to obtain the desired ratio of diastereoisomers. Preferably, the substantially diastereoisomerically pure salts according to the invention have a diastereoisomeric excess greater than 96%, more preferably greater than 97%, most preferably greater than 98%.

Preferably, substantially enantiomerically pure (R)- or (S)-2-[4-(4-chlorobenzhydryl)piperazin-1-yl]-ethoxyacetamide obtained according to the present invention have an enantiomeric excess greater than 96%, more preferably greater than 97%, most preferably greater than 98%.

According to another embodiment the invention provides a process for preparing a substantially enantiomerically pure (R) or (S)-2-[4-(4-chlorobenzhydryl)piperazin-1-yl]-ethoxyacetamide.

It has been noted, surprisingly, that the process according to the present invention makes it possible to obtain, in an industrial plant, (S) or (R)-2-[4-(4-chlorobenzhydryl)piperazin-1-yl]-ethoxyacetamide with a very high production efficiency, and allows the separation of up to 270 g of substantially enantiomerically pure (R)-2-[4-(4-chlorobenzhydryl) piperazin-1-yl]-ethoxyacetamide per kg from a racemic mixture of (R) and (S)-2-[4-(4-chlorobenzhydryl)piperazin-1-yl]-ethoxyacetamide.

The amount of an enantiomer with respect to another is conveniently expressed as the percent enantiomeric excess, which is abbreviated "% ee". The percent enantiomeric excess can be calculated as follows:

% ee=[([A]−[B]):([A]+[B])]×100, where [A] is the concentration of one of the enantiomers, and [B] is the concentration of the other enantiomer. In a completely resolved material, the enantiomeric excess is equal in weight to the total material so that % ee is 100%. In this case the optical purity of the compound will be 100%. The concentration of each of the enantiomers is, of course, expressed on the same basis, and can be expressed on either a weight of molar basis because the enantiomers have the same molecular weight.

The chiral HPLC method used to determine the optical purity is as follows:

About the sample was dissolved in the mobile phase and the concentration was adjusted so as to be about 1 mg/mL.

Detector: UV light absorption photometer (210 nm)
Column: Daicel Chiralpak AD 10 μm 250×4.6 mm
Column temperature: Room temperature
Mobil phase: n-Hexane/Isopropanol (50:50)
Flow rate: 1 mL/min Range of peak measurement: range within 20 minutes after the injection of the sample.

Retention time: (R)-2-[4-(4-chlorobenzhydryl)piperazin-1-yl]-ethoxyacetamide about 6 to 8 minutes.

Retention time: (S)-2-[4-(4-chlorobenzhydryl)piperazin-1-yl]-ethoxyacetamide about 11 to 15 minutes.

The amount of the (R)-isomer (%) was calculated by the following equation amount of $$(R)\text{-isomer}(\%) = \frac{P^R}{P^R + P^S} \times 100$$

$P^R$: percentage of peak area of (R)-isomer
$P^S$: percentage of peak area of (S)-isomer.

The examples which follow illustrate the process according to the present invention and show operating details with reference to preferred embodiments of the invention, it being clearly understood that the invention is not limited to these specific operating conditions.

EXAMPLE 1

Preparation of substantially diastereomerically pure (R)-[2-[4-(4-chlorobenzylhydryl)piperazin-1-yl] ethoxyacetamide-(S)-pyrrolidone-5-carboxylic acid salt from racemic 2-[4-(4-chlorobenzhydryl)piperazin-1-yl]-ethoxyacetamide and (S)-pyrrolidone-5-carboxylic acid In a 3 L double-jacket glass reactor, (S)-pyrrolidone-5-carboxylic acid (100 g-0.775 mol), a racemic mixture of 2-[4-(4-chlorobenzhydryl)piperazin-1-yl]-ethoxyacetamide (300 g-0.775 mol) and 1200 mL of an AcOEt-MeOH (acetate ethyl 4:methanol 1) mixture were introduced. The reaction medium was refluxed until the complete dissolution of the solid was observed. The reaction medium was then cooled down to 20° C. in 11 hours, then it was stirred at 20° C. for 24 hours. After filtration, the solid washed with 2×250 mL of an AcOEt-MeOH (9:1) mixture. The weight of the wet solid, i.e. partially diastereoisomerically enriched (R)-2-[4-(4-chlorobenzhydryl)piperazin-1-yl]-ethoxyacetamide-(S)-pyrrolidone-5-carboxylic acid salt, was 165.6 g.

150 g of partially diastereoisomerically enriched (R)-2-[4-(4-chlorobenzhydryl)piperazin-1-yl]-ethoxyacetamide-(S)-pyrrolidone-5-carboxylic acid salt were reintroduced into a 3 L double-jacket glass reactor with 600 mL of AcOEt-MeOH (4:1). The mixture was refluxed for 2 hours and was allowed to cool down at 20° C. in 12 hours. After 5 hours at 20° C., the crystals were filtered, washed with AcOEt-MeOH (9:1) (250 mL). The weight of the dried crystals was 102 g.

The yield of substantially diastereomerically pure (R)-2-[4-(4-chlorobenzhydryl)piperazin-1-yl]-ethoxyacetamide-(S)-pyrrolidone-5-carboxylic acid salt is of 27% (in respect to a maximal yield of 50%).

Diastereomeric excess: 96%
Melting point: 159.5° C.
1H NMR (dmso d6) δ (ppm) 7.85 (broad s, 1H), 7.52 (broad s, 1H), 7.40-7.14 (m, 9H), 4.29 (s, 1H), 4.02 (1H, m), 3.78 (s, 2H), 3.54 (t, 2H), 2.60-2.57 (m, 4H), 2.40-2.20 (m, 4H), 2.07-2.16 (m, 2H), 1.96 (m, 1H).

EXAMPLE 2

Preparation of substantially enantiomerically pure (R)-[2-[4-[(4-chlorophenyl)phenylmethyl]-1-piperazinyl]ethoxy]acetamide from substantially diastereoisomerically pure (R)-2-[4-(4-chlorobenzhydryl) piperazin-1-yl]-ethoxyacetamide-(S)-pyrrolidone-5-carboxylic acid salt 25 g of the crystals mentioned above were dispersed in a water-toluene suspension followed by the addition of 10 g of 50% NaOH. The mixture was stirred magnetically at room temperature until the homogeneity of the two layers was observed. The reaction mixture was transferred into a 1 L separation funnel and the organic and aqueous layers were allowed to decant. The aqueous layer was then extracted three times by 100 mL of toluene, the organic layers were collected and washed twice with water. The solvent was distilled off at reduced pressure to afford substantially enantiomerically pure (R)-2-[4-(4-chlorobenzhydryl)piperazin-1-yl]-ethoxyacetamide as an oil compound which crystallised upon standing. Yield: 20 g (yield: 100%).

Enantiomeric excess=96%

1H NMR (dmso d6) δ (ppm) 7.80 (broad s, 1H), 7.36-7.14 (m, 9H), 6.43 (broad s, 1H), 4.20 (s, 1H), 3.92 (s, 2H), 3.57 (t, 2H), 2.54-2.51 (m, 4H), 2.37-2.30 (m, 4H)

We obtained a substantially enantiomerically/diastereomerically pure product having the required optical purity for a pharmaceutical application, which is of 96% for the present application.

The invention claimed is:

1. A compound selected from
   (S)-2-[4-(4-chlorobenzhydryl)piperazin-1-yl]-ethoxyacetamide-(S)-pyrrolidone-5-carboxylic acid salt,
   (R)-2-[4-(4-chlorobenzhydryl)piperazin-1-yl]-ethoxyacetamide-(S)-pyrrolidone-5-carboxylic acid salt,
   (S)-2-[4-(4-chlorobenzhydryl)piperazin-1-yl]-ethoxyacetamide-(R)-pyrrolidone-5-carboxylic acid salt, or
   (R)-2-[4-(4-chlorobenzhydryl)piperazin-1-yl]-ethoxyacetamide-(R)-pyrrolidone-5-carboxylic acid salt.

2. A compound according to claim 1 which compound is substantially diastereoisomerically pure.

3. A process for preparing (S)-2-[4-(4-chlorobenzhydryl)piperazin-1-yl]-ethoxyacetamide or (R)-2-[4-(4-chlorobenzhydryl)piperazin-1-yl]-ethoxyacetamide, comprising chemical resolution of a mixture of (R) and (S)-2-[4-(4-chlorobenzhydryl)piperazin-1-yl]-ethoxyacetamide in the presence of (S)-pyrrolidone-5-carboxylic acid or (R)-pyrrolidone-5-carboxylic acid.

4. The process according to claim 3 wherein the chemical resolution is performed in the presence of a solvent or a mixture of solvents.

5. The process according to claim 4 wherein the solvent is a mixture of ethyl acetate and methanol.

6. The process according to claim 3 wherein the (S)-2-[4-(4-chlorobenzhydryl)piperazin-1-yl]-ethoxyacetamide and (R)-2-[4-(4-chlorobenzhydryl)piperazin-1-yl]-ethoxyacetamide are substantially pure.

7. The process according to any of claims 3-5 or 6 wherein the mixture of (R) and (S)-2-[4-(4-chlorobenzhydryl)piperazin-1-yl]-ethoxyacetamide is a racemic mixture.

* * * * *